United States Patent [19]

Lauderdale

[11] Patent Number: 5,743,853
[45] Date of Patent: Apr. 28, 1998

[54] SERRATED S-RETRACTOR

[76] Inventor: Robert A. Lauderdale, #2 Crown Pl., Richardson, Tex. 75080

[21] Appl. No.: 708,842

[22] Filed: Sep. 9, 1996

[51] Int. Cl.⁶ .................................................. A61B 11/02
[52] U.S. Cl. .................................... 600/210; 600/217
[58] Field of Search .............................. 600/201, 204, 600/206, 208, 209, 210, 211, 217, 235; 606/190, 191

[56] References Cited

U.S. PATENT DOCUMENTS 4,610,243  9/1986  Ray ..................................... 600/217 X
4,616,633  10/1986  Vargas et al. ....................... 600/210 X
4,747,394  5/1988  Watanabe ............................ 600/217 X

*Primary Examiner*—Beverly M. Flanagan
*Attorney, Agent, or Firm*—Daniel V. Thompson

[57] ABSTRACT

An apparatus for use in surgery includes an instrument body having a middle portion and first and second ends. The instrument body is S-shaped along its length, with the middle portion being straight. At least one of the first or second ends is serrated for use in dissection of tissue.

1 Claim, 1 Drawing Sheet

SERRATED S-RETRACTOR

TECHNICAL FIELD

This application relates to surgical instruments, and more particularly to an S-retractor useful in laparoscopic surgery.

BACKGROUND ART

The conventional S-retractor used in laparoscopic surgery has identical rounded ends. While such device is useful for its intended purpose, it has been found that other instruments are required to dissect tissue during surgery. Thus, there presently exists a need for an S-retractor that is useful in the conventional manner, but also provides the ability to dissect tissue with the same instrument.

SUMMARY OF THE INVENTION

The present invention provides an S-retractor having a specially-adapted serrated end for dissection of tissue.

BRIEF DESCRIPTION OF THE DRAWINGS

A more complete understanding of the invention and its advantages will be apparent from the Detailed Description taken in conjunction with the accompanying Drawings, in which.

DETAILED DESCRIPTION OF THE PREFERRED EMBODIMENT

Referring initially to FIGS. 1–4, where like numerals indicate like and corresponding elements, instrument 10 includes an instrument body 12 having a middle portion 14 and first and second ends 16, 18. Preferably, instrument body 12 is formed of a strip about ten inches long, about ⅜ inch wide, and about 1/16 inch thick. Typically, the metal of manufacture will be stainless steel or hard plastic. The ⅜ inch wide dimension of the strip is referred to as the "wide direction" herein, and is the dimension shown in FIG. 3.

Figure 4:
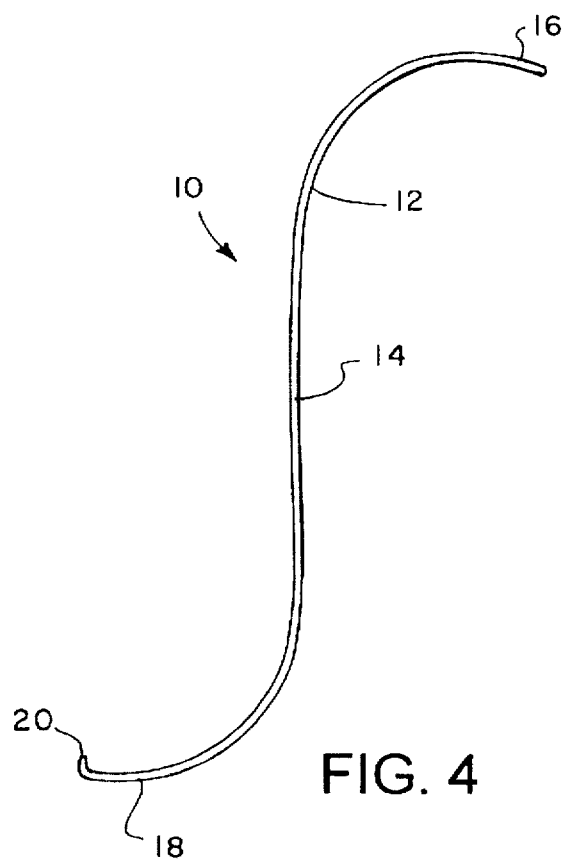
FIG. 4 is a second side view of the invention, rotated 90° from FIG. 3.

Instrument body 12 is S-shaped along its length, as best shown in FIG. 4. Middle portion 14 is straight. First end 16 is circularly bent from the middle portion 14, as best shown in FIG. 4, about 100°. In contrast, second end 18 is circularly bent about 90° in the opposite direction from the first end 16, again as best shown in FIG. 4. First end 16 is rounded in the wide direction, in accordance with the conventional S-retractor of the prior art as shown in phanthom in FIG. 3 and in perspective in FIG. 1.

Figure 1:
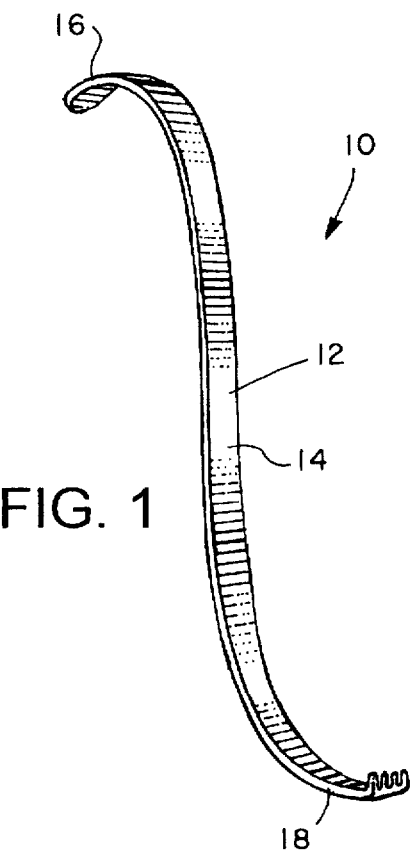
FIG. 1 is a perspective view of the invention.
Figure 2:
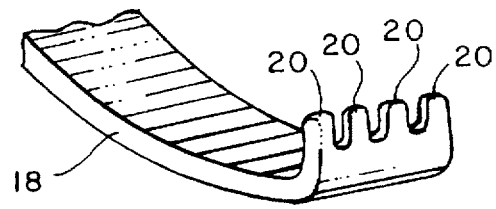
FIG. 2 is an enlarged view of the serrated end.
Figure 3:
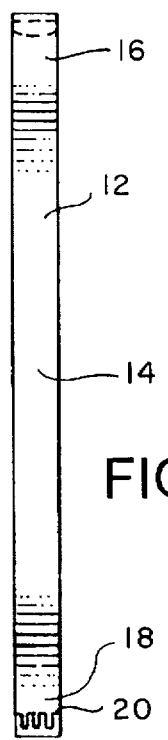
FIG. 3 is a first side view of the invention.

The key feature of the invention is second end 18 being serrated in the wide direction, as best shown in FIG. 2. Preferably second end 18 has four teeth 20, extending perpendicularly, as shown in FIG. 4, from second end 18 in a direction parallel to and spaced apart from the middle portion 14. The teeth 20 extend in a direction generally towards the middle portion, as shown in FIG. 4.

In the preferred embodiment, the four teeth 20 are about 1/16 inch wide, about ⅛ inch long and about 1/16 inch apart.

In operation, the S-retractor is useful in the conventional manner using the rounded first end, however, when the need arises to dissect tissue, the surgeon may easily rotate the tool to switch ends, and immediately begin dissecting tissue without having to change instruments.

Whereas, the present invention has been described with the respect to a specific embodiment thereof, it will be understood that various changes and modifications will be suggested to one skilled in the art, and it is intended to encompass such changes and modifications as fall within the scope of the appended claims.

I claim:

1. Apparatus for use in surgery, comprising:

an instrument body being formed of a strip of metal about 10 inches long, about ⅜ inch wide, and about 1/16 inch thick;

the instrument body having a middle portion and first and second ends;

the instrument body being S-shaped along its length, with the middle portion being straight, and the first end being circularly bent from the middle portion about 100 degrees, the second end being circularly bent about 90 degrees in the opposite direction from the first end;

the first end being rounded in the wide direction; and the second end being specially adapted for tissue dissection, by being serrated in the wide direction, with four teeth about 1/16 inch wide, about ⅛ inch long and about 1/16 inch apart, the teeth extending perpendicularly from the second end in a direction parallel to and spaced apart from the middle portion, and the teeth extending in a direction generally towards the middle portion.

* * * * *